US007264962B1

(12) United States Patent
Simmons et al.

(10) Patent No.: US 7,264,962 B1
(45) Date of Patent: Sep. 4, 2007

(54) ENZYMATIC CASCADE BIOREACTOR

(75) Inventors: Blake A. Simmons, San Francisco, CA (US); Joanne V. Volponi, Livermore, CA (US); David Ingersoll, Albuquerque, NM (US); Andrew Walker, Woodinville, WA (US)

(73) Assignee: Sandia Corporation, Livermore, CA (US)

( * ) Notice: Subject to any disclaimer, the term of this patent is extended or adjusted under 35 U.S.C. 154(b) by 361 days.

(21) Appl. No.: 11/080,901

(22) Filed: Mar. 14, 2005

(51) Int. Cl.
*C12M 1/00* (2006.01)
*C12M 1/24* (2006.01)
*C12M 1/18* (2006.01)

(52) U.S. Cl. .................. 435/293.1; 435/94; 435/105; 435/289.1; 435/291.4; 435/304.1

(58) Field of Classification Search .............. 435/94, 435/105, 289.1, 291.4, 293.1, 304.1
See application file for complete search history.

(56) References Cited

U.S. PATENT DOCUMENTS

| | | | |
|---|---|---|---|
| 4,276,379 A | 6/1981 | Heady | 435/94 |
| 4,384,045 A | 5/1983 | Ho et al. | 435/176 |
| 4,774,183 A | 9/1988 | Fan | 435/105 |
| 4,797,358 A | 1/1989 | Motai et al. | 435/176 |
| 4,861,381 A | 8/1989 | Paul et al. | 127/41 |
| 5,234,991 A | 8/1993 | Tayot et al. | 525/54.1 |
| 5,314,810 A | 5/1994 | Kono et al. | 435/97 |
| 5,314,814 A | 5/1994 | Harder et al. | 435/177 |
| 5,397,700 A | 3/1995 | Fournier et al. | 435/41 |
| 5,476,776 A | 12/1995 | Wilkins | 435/105 |
| 5,998,177 A | 12/1999 | Catani et al. | 435/101 |
| 5,998,183 A | 12/1999 | Le Fevre et al. | 435/176 |
| 6,013,491 A | 1/2000 | Martinez | 435/105 |
| 6,294,281 B1 | 9/2001 | Heller | 429/43 |
| 6,500,571 B2 | 12/2002 | Liberatore et al. | 429/2 |
| 6,503,648 B1 | 1/2003 | Wang | 429/21 |
| 6,660,502 B2 | 12/2003 | Catani et al. | 435/101 |
| 6,686,075 B2 | 2/2004 | Gieshoff et al. | 429/2 |
| 6,706,188 B2 | 3/2004 | Carlsson et al. | 210/635 |
| 2001/0055793 A1* | 12/2001 | Catani et al. | 435/101 |

OTHER PUBLICATIONS

Soykan, O.; "Power Sources for Implantable Medical Devices"; *Business Briefing: Medical Device Manufacturing & Technology*, 2002 *Device Technology & Applications—Electronics* http://www.bbriefings.com/cdps/cditem.cfm?NID=753.
Heller, A. ;"Miniature biofuel cells," *Physical Chemistry Chemical Physics*, v.6(2), pp. 209-216, Jan. 21, 2004.
Volponi, J. V.; Simmons, B. A.; Walker, A.; Ingersoll, D.; "Bio-Reforming Fuels for a Biofuel Cell," *The Electrochemical Society*, 205th Meeting, San Antonio, TX, Abs. #673, May 11, 2004.
Kim, H.-H.; Mano, N.; Zhang, Y.; Heller, A.; "A Miniature Membrane-less Biofuel Cell Operating under Physiological Conditions at 0.5 V," *Journal of the Electrochemical Society*, v.150(2), pp. A209-A213, 2003.
Gouda, M. D.; Thakur, M. S.; Karanth, N. G.; "Optimization of the multi-enzyme system for sucrose biosensor by response surface methodolgy," *World Journal of Microbiology and Biotechnology*, v. 17(5), pp. 595-600, 2000.
Gouda, M. D.; Kumar, M. A.;Thakur, M. S.; Karanth, N. G.; "Enhancement of Operational stability of an enzyme biosensor for glucose and sucrose using Protein based stabilizing agents," *Biosensors and Bioelectronics*, v.17, pp. 503-507, 2002.
Mano, N.; Mao, F.; Heller, A. ; "Miniature Biofuel Cell Operating in a Physiological Buffer," *Journal of the American Chemical Society*, v.124, pp. 12962-12963, 2002.
Mousty, C.; Cosnier, S.; Shan, D.; Mu, S.; "Trienzymatic biosensor for the Determination of inorganic phosphate," *Analytica Chimica Acta*, v. 443, pp. 1-8, 2001.
Chen, t.; Barton, S. C.; Binyamin, G.; Gao, Z.; Zhang, Y.; Kim, H.-H.; Heller, A.; "A Miniature Biofuel Cell," *Journal of the American Chemical Society*, v. 123, pp. 8630-8631, 2001.
Eshkenazi, I.; Maltz, E.; Zion, B.; Rishopn, J.; "A Three-Cascaded-Enzyme Biosensor to Determine Lactose Concentration in Raw Milk," *Journal of Dairy Science*, v. 83, pp. 1939-1945, 2000.
Woodward, J.; Orr, M.; "Enzymatic Conversion of Sucrose to Hydrogen," *Biotechnology Progress*, v.14, pp. 897-902, 1998.
Mizutani, F.; Yabuki, S.; "Rapid determination of glucose and sucrose by an amperometric glucose-sensing electrode combined with an invertase/mutarotase-Attached measuring cell," *Biosensors & Bioelectronics*, v. 12(9-10), pp. 1013-1020, 1997.

* cited by examiner

*Primary Examiner*—Herbert J. Lilling
(74) *Attorney, Agent, or Firm*—Timothy P. Evans

(57) ABSTRACT

Disclosed is an apparatus and method for continuously converting sucrose to β-D-glucose. The method comprises a three stage enzymatic reactor in which an aqueous solution of sucrose is first converted into a solution of fructose and α-D-glucose by passing it through a porous, packed column containing an inert media on which invertase is immobilized. This solution is then sent through a second packed column containing glucose isomerase and finally a third packed column containing mutarotase. Solution temperature and pH are adjusted to maximize glucose output.

22 Claims, 6 Drawing Sheets

ENZYMATIC CASCADE BIOREACTOR

STATEMENT OF GOVERNMENT INTEREST

This invention was made with Government support under government contract DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND OF THE INVENTION

1. Field of the Invention

Embodiments of the present invention relate generally to a bioreformation of complex to produce glucose as a fuel. More particularly, the present invention relates to a bioreactor for converting sucrose or fructose into glucose through an enzymatic cascade process within a series of packed columns.

2. Related Art

In recent years implanted therapeutic medical devices have become increasingly important. Devices such as cardiac and brain pacemakers, insulin and chemotherapy pumps, left ventricular assist devices ("LVAD"), cochlear implants, and various implanted blood sensors are routinely used to assist patients who are chronically ill. These devices, however, require a source of power, typically implanted batteries which must be removed and replaced periodically. Because battery replacement can place the user in medical jeopardy, use of fuel cells, wherein the body's own supply of glucose sugar is utilized as the energy source, has been a current area of active investigation (e.g., U.S. Pat. Nos. 6,294,281 and 6,503,648).

However, one of the primary limitations of biologically inspired fuel cells is the quantity and quality of fuel feedstock that can be provided to it. In those applications where only complex sugars such as sucrose or fructose, are available instead of glucose, an efficient means for converting sucrose or fructose to glucose would be advantageous. This converter output would then serve as a fuel stream input to power a mechanical/electrical device.

The present concept, therefore, discloses an enzymatic cascade approach for direct reduction of sucrose and fructose into glucose. The design is based on a "flow-through" fuel reformation reactor which utilizes an enzymatic "cascade" for converting sucrose and fructose into glucose. The approach uses three packed columns linked in series wherein an inlet stream comprising a sucrose solution first passes through a matrix comprising invertase which converts the sucrose to a solution comprising fructose and $\alpha$-D-glucose. This converted solution then passes through a second matrix comprising glucose isomerase which converts the fructose into, $\beta$-D-glucose. Lastly, the solution passes through a third matrix comprising mutarotase which converts the $\alpha$-D-glucose fraction to, $\beta$-D-glucose. The three matrices comprising the three immobilized enzymes are flow-through columns packed with a plurality of porous silica particles whose surfaces have been modified so as to bind to amine sites on each of the enzymes, thereby immobilizing each specific enzyme-type to the silica particle surfaces.

This approach enables deploying a glucose-based fuel cell into environments that possess an abundance of sucrose and/or fructose but have minimal glucose (i.e., plants, trees). Moreover, the concept of an enzymatic cascade is also relevant in the field of alternative fuel production (ethanol and carbon sequestration, where the use of such a system could prove to be revolutionary in terms of process engineering, cost benefit, and efficiency.

Related art comprise patents to Catani, et al. (U.S. Pat. Nos. 6,660,502, and 5,998,177) who disclose a process for forming glucose and fructose from sucrose wherein an enzyme is immobilized by absorption on a granular carrier having a primary to quaternary amine, and wherein the carrier is an epoxy polymer, a vinyl polymer, or a chitosan derivative having a primary, secondary or tertiary amine. Further, Tayot, et al., (U.S. Pat. No. 5,234,991) discloses a porous support such as silica which is coated with an aminated polysaccharide polymer; Le Favre, et al., (U.S. Pat. No. 5,998,183) disclose a method for immobilizing enzymes on silica gels and alumino-silicates using glutaraldehyde; and Ho, et al., (U.S. Pat. No. 4,384,045) disclose a method for activating the surface of siliceous surfaces to improve attachments of enzymes. Lastly, Wilkins (U.S. Pat. No. 5,476,776) discloses an electrochemical sensor utilizing enzymes immobilized on particulate matter including silicon and aluminum oxides.

SUMMARY

Disclose herein is a method for converting simple sugars from more complex sugars for use as a bio-fuel. This is realized by establishing a "flow-through" reactor system that contains a porous media onto which enzymes capable of converting complex sugars to simple sugars are immobilized.

It is an object of this invention, therefore, to provide a bioreactor for bioreformation of any complex sugar to simple sugars.

Yet another object of this invention is a bioreactor containing a porous media packing contained within one or more flow channels.

It is another object of this invention wherein the porous media is permeable to a liquid elutant containing complex sugars dissolved therein.

It is a further object of this invention to provide a bioreactor wherein enzymes are immobilized into the porous bed media through established surface chemistry techniques.

It is yet another object of this invention to provide a bioreactor for creating an enzymatic cascade reaction wherein through a systematic continuum of reactions, a simple sugar is produced and discharged in the system output stream.

It is yet another object of this invention that the enzymatic cascade can be applied to alternative bio-fuels that require reformation before use in a fuel cell. These include, but are not linked to, fatty acids, triglycerides, cholesterols, urea, and the like.

DETAILED DESCRIPTION

We disclose herein a method and an apparatus for biologically converting, or "reforming," complex sugars into simple sugars through an enzymatic cascade process. This approach is realized by providing a flow-through reactor system that contains a porous media onto which various enzymes, capable of converting complex sugars to simpler sugars, are immobilized. The porous media-comprises a plurality of 7-10 μm silica beads obtained from Alltech Associates Inc., (Deerfield, Ill.) and contained within a glass chromatography column (3.3 mm bore, 50 mm in length) obtained from Omnifit Ltd. (Cambridge, United Kingdom), and having a bead volume of about 0.35 ml to form a "packed bed" that is permeable to a liquid elutant containing the complex sugars dissolved therein. Through a systematic continuum of reactions, a simple sugar is produced and discharged in the system outlet stream.

Figure 1:
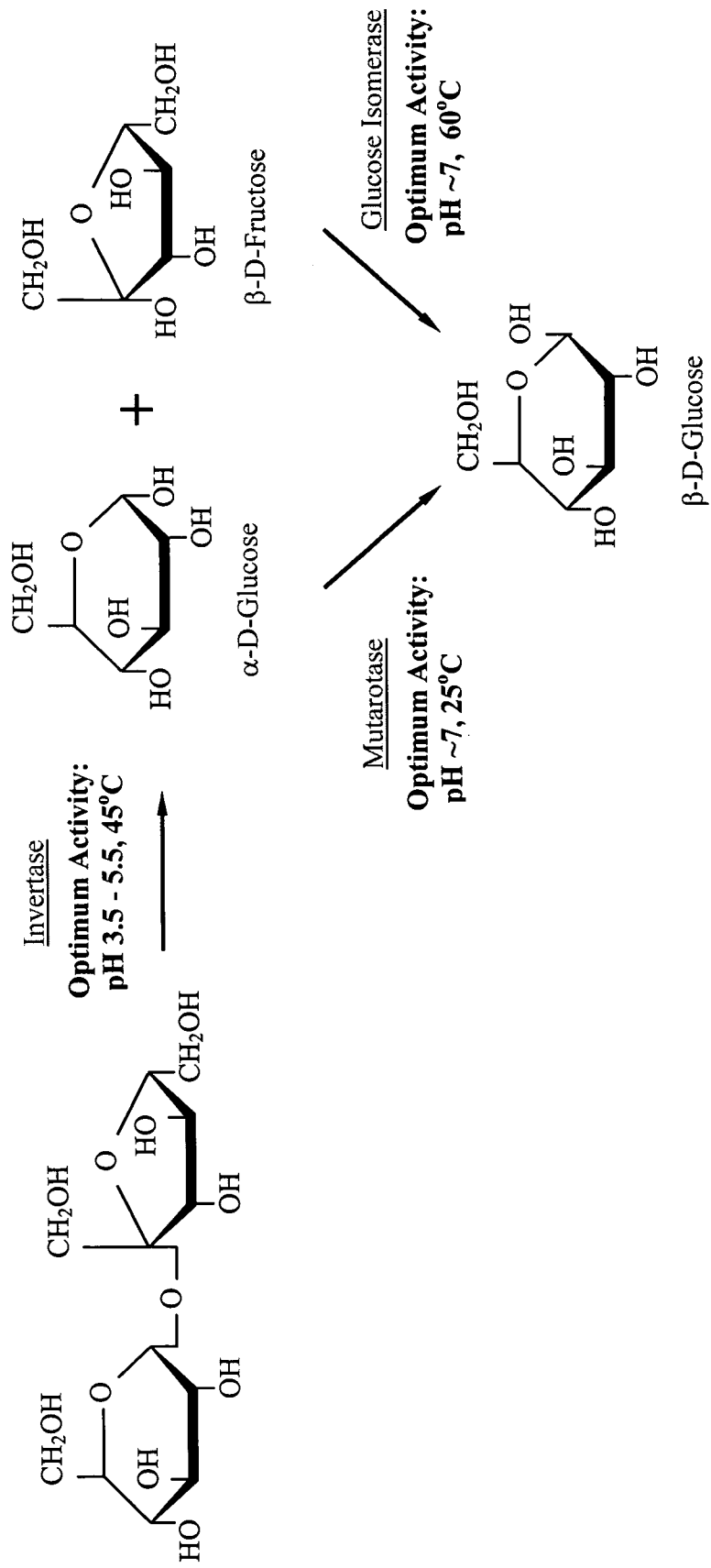
FIG. 1 shows the enzymatic cascade utilized in the embodiments of the present invention which provides for the conversion of sucrose into glucose, and the corresponding reaction pathways and products.

The overall strategy comprised a conversion of a sucrose solution first to β-D-fructose and α-D-glucose followed by conversion of the β-D-fructose in the elutant stream to β-D-glucose followed by conversion of the α-D-glucose in the elutant stream into β-D-glucose. A schematic representation of a reformation cascade that has been reduced to practice is shown in FIG. 1. This approach is achieved through the use of three separate enzyme packed columns attached in series.

Each of the column stages contains the appropriate enzyme to achieve the sought after conversion product for that stage. As mentioned, the various enzymes are immobilized onto the media contained within each column since each must have a surface onto which it is fixed or each would simply wash through the column along with the elutant solution. The enzymes, therefore, are immobilized into the porous media through established surface chemistry techniques. However, in order for the bed to be effective, a methodology must be used that links the enzymes to the silica beads strongly enough that they remain fixed and active throughout the conversion process and for many iterations thereafter.

Figure 2:
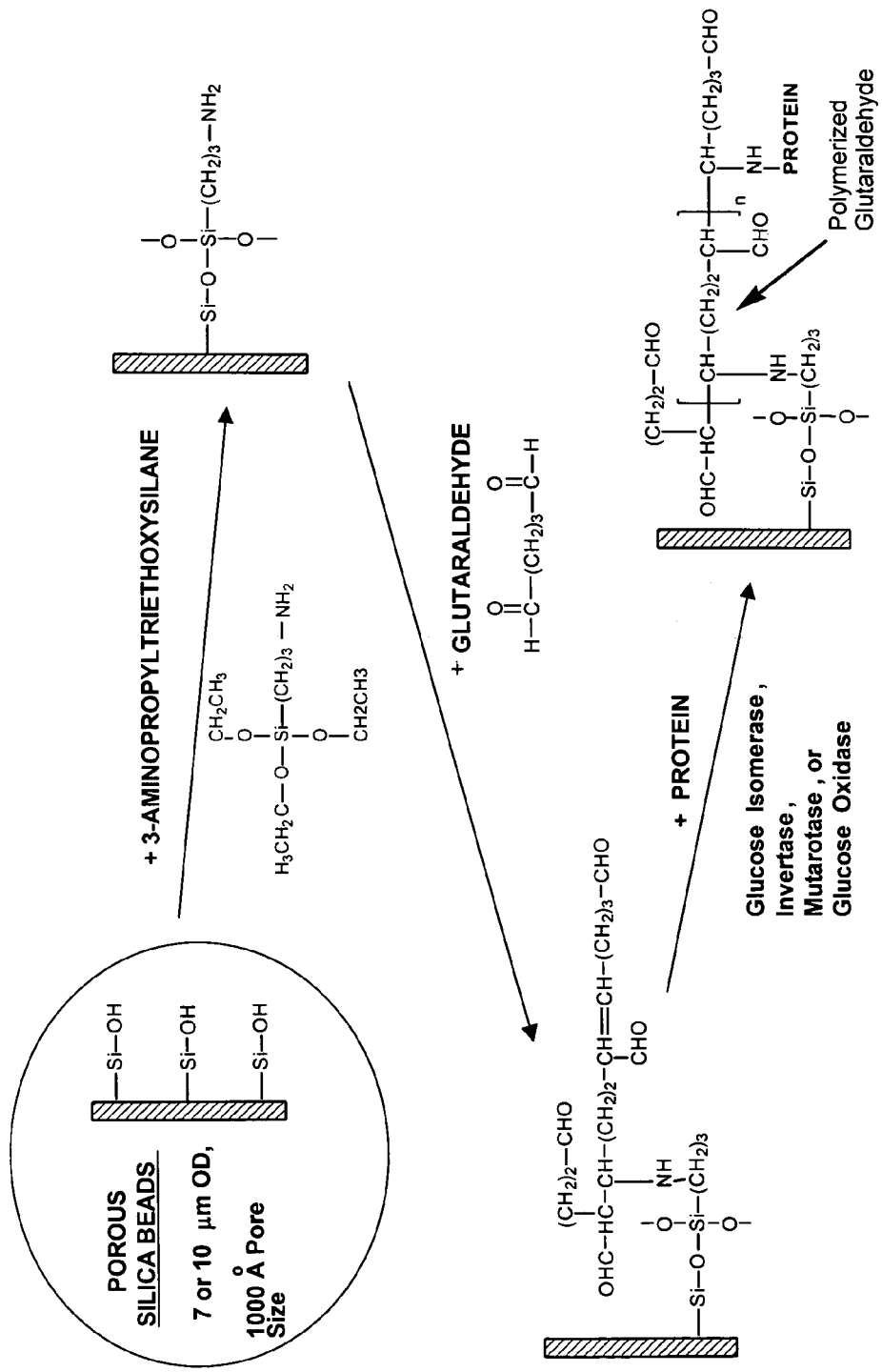
FIG. 2 shows the general methodology for immobilizing enzymes on silica beads.

We have utilized the general procedure, shown in FIG. 2, which has been proven to be robust and effective for all of the enzymes studied. It comprises silanating the native surface of the silica beads and then attaching amine groups using an amino-functional silane. This aminated silica surface is then further functionalized with the addition of glutaraldehyde, an amine group cross-linker having a terminal aldehyde group reacting with the primary amino groups of the attached amino-functional silane, through an imine bond. This combination of surface modification allows for directly tethering the enzymes to the bead surfaces at relatively high loading conditions (about 25 to about 43 μg of enzyme per mg of silica beads) resulting in enzyme coated beads that can be easily packed into a flow-through column using standard laboratory practices.

Useful amino-functional silanes include: aminopropyltriethoxysilane, aminopropyltrimethoxysilane, aminopropylmethyldiethoxysilane; aminopropylmethyldimethoxysilane; aminoethylaminopropyltriethoxysilane; aminoethylaminopropyltrimethoxysilane; aminoethylaminopropylmethyldimethoxysilane; diethylenetriaminopropyltriethoxysilane; diethylenetriaminopropyltrimethoxysilane; diethylenetriaminopropylmethyldiethoxysilane; diethylenetriaminopropylmethyldimethoxysilane; cyclohexylaminopropyltrimethoxysilane; haxanedoaminomethyltriethoxysilane; phenylaminomethyltriethoxysilane; phenylaminomethyltrimethoxysilane; diethylaminomethyltriethoxysilane; (dimethylaminomethyl)methyldimethoxysilane; and methylaminopropyltrimethoxysilane. Of these, 3-aminopropyltriethoxysilane is preferred.

Useful amine group cross-linkers include formaldehyde, glutaraldehyde, mono- and di-aldehyde PEG, and bis(imido esters), bis(succinimidyl esters), diisocyanates and diacid chlorides. Glutaraldehyde, however, is preferred.

In particular, as shown in FIG. 2, beads are slurry packed in a cylindrical column through which the bioreformation reactions will take place. Typical column packing involves the use of pressure and time to reach satisfactory conditions, during which the enzyme may be dislodged or destroyed. During and after column packing, therefore, care must be taken and the process monitored to ensure that each enzyme remains immobilized and is still active after the packing process. This is done by handling the enzyme coated beads and storing the packed columns in a buffer solution having pH conditions that are optimal for each enzyme, storing the packed columns at a temperature of 4° C., and by adding an $Mg^+$ stabilizer to the column containing the glucose isomerase. The invertase packed column was maintained in a buffer at a pH of about 5, and the glucose isomerase and mutarotase packed columns were maintained in a buffer at a pH of about 7.

Figure 3:
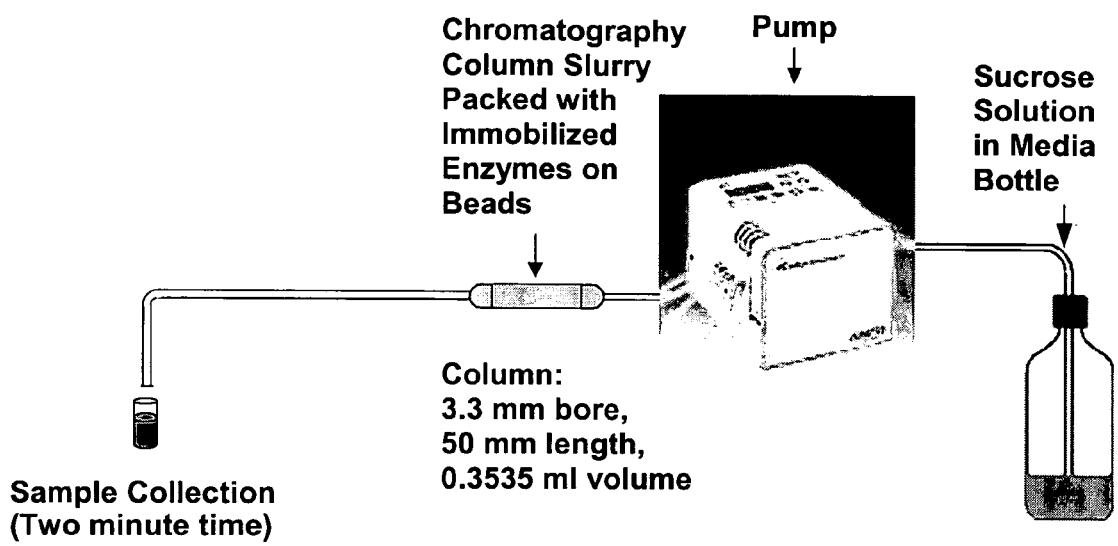
FIG. 3 illustrates a schematic of the apparatus used to pump liquids through the column and collect samples. Each sample is taken as a two-minute fractionation of the column effluent.

As each of the enzymes used in our process has been optimized through evolution to operate with its highest activity in a narrow range of conditions; as these conditions are presumably not the same for each enzyme, we separately tested each of the enzymes to establish the optimal temperature, pH, and buffer conditions for the incoming elutant stream. A representative example of the apparatus used in these evaluations is presented in FIG. 3.

Figure 4:
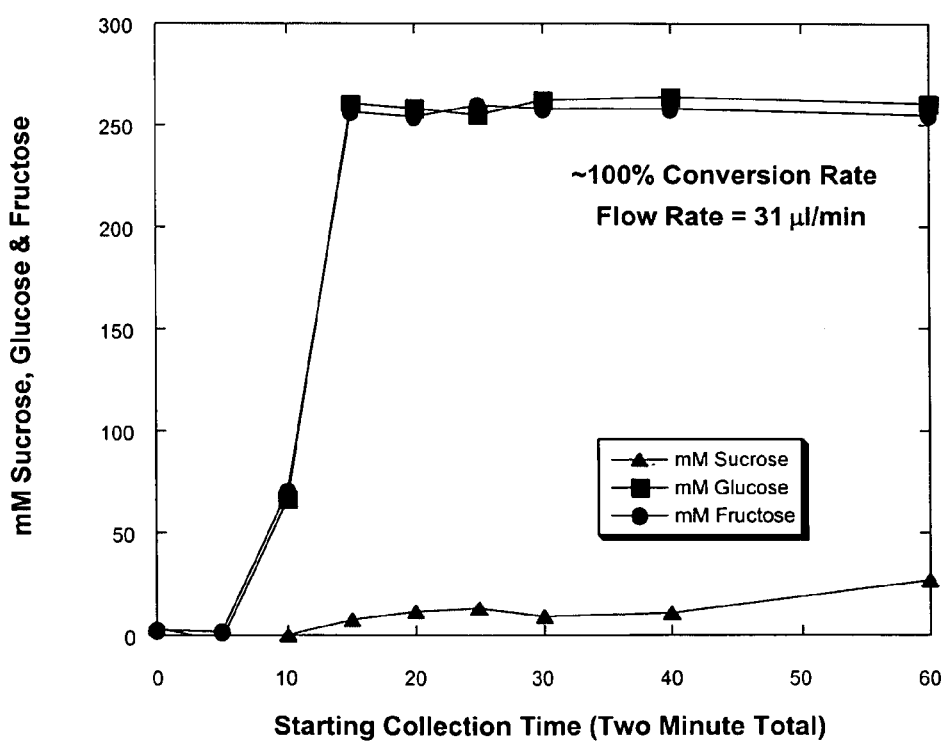
FIG. 4 shows the process of sucrose conversion achieved with a column containing the enzyme invertase.

We, therefore, evaluated the response of each of our enzyme columns at a variety of conditions. This included testing each enzyme column under changing sugar solution concentrations, changing pH conditions, changing flow rate through the column, and changing temperature of the column and sugar solution. TABLE 1 below provides a listing of the concentration of sucrose, glucose and fructose in the output stream obtained from a column of the present invention containing the enzyme invertase. FIG. 4 presents this data graphically and shows the rapid conversion of sucrose to glucose and fructose. The incoming elutant stream comprised an aqueous solution of 250 mM sucrose, at a pH of 4.6 and heated to 45° C.±2° C. The observed conversion rate was found to be about 100% for this process step.

TABLE 1

Measured Concentration of Sucrose, Glucose and Fructose in Output Stream of the Invertase Column

| Collection Time (sec) | Sucrose Concentration (mM) | Glucose Concentration (mM) | Fructose Concentration (mM) |
|---|---|---|---|
| 0 | 3.7 | 0.0 | 2.6 |
| 5 | 0.0 | 0.0 | 1.8 |
| 10 | 0.2 | 66.0 | 70.3 |
| 15 | 7.2 | 260.7 | 70.4 |
| 20 | 11.7 | 258.2 | 254.3 |
| 25 | 13.0 | 255.2 | 259.7 |
| 30 | 9.0 | 261.8 | 258.2 |
| 40 | 10.3 | 263.7 | 258.0 |
| 50 | 20.6 | 294.9 | 284.6 |
| 60 | 26.9 | 260.4 | 255.1 |

Figure 5:
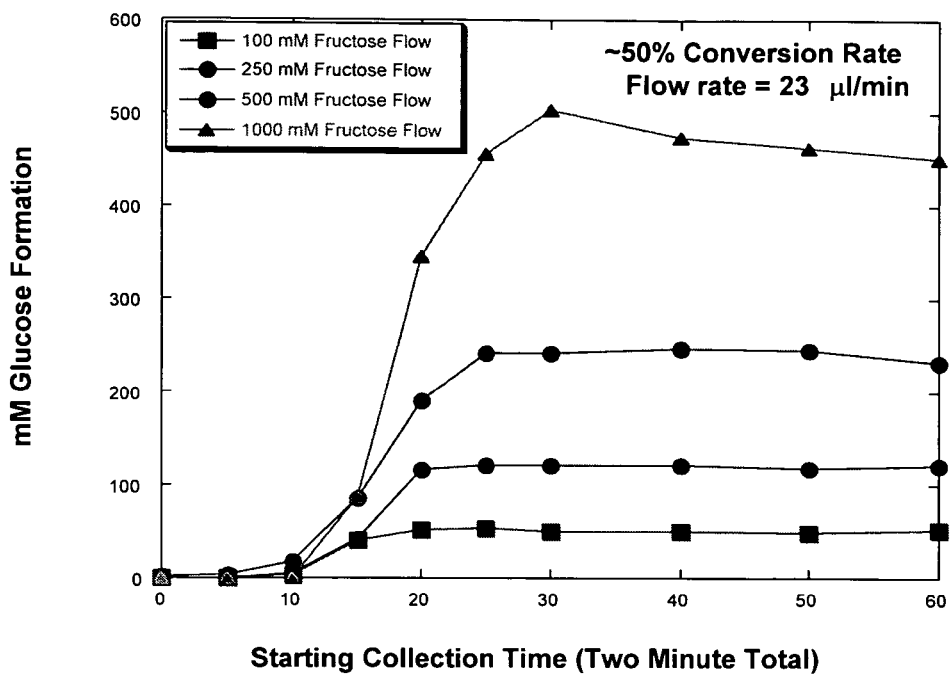
FIG. 5 shows the process of fructose conversion achieved with a column containing the enzyme glucose isomerase.

The conversion of fructose was achieved with a second column of the present invention containing the enzyme glucose isomerase. FIG. 5 presents a summary of the data, shown in TABLE 2, showing the concentration of glucose formation in the column output stream where the incoming elutant stream comprised fructose, at widely different initial concentrations, in an aqueous pH 6.8 buffer with 20 mM $MgCl_2$, and heated at a temperature of 60° C.±2° C. ($MgCl_2$ is added to the buffer solution because $Mg^+$ ions act as an activator and stabilizer for the glucose isomerase.) Glucose was determined in samples collected at specific intervals of time as depicted in FIG. 5. As shown in TABLE 2 below, the typical conversion rates obtained were found to average above 50%.

TABLE 2

Measured Concentration of Glucose in the Output Stream of the Glucose Isomerase Column at Several Different Initial Fructose Concentrations

| Collection Time | mm Glucose Formed from Fructose Having an Input Concentration of: | | | |
|---|---|---|---|---|
| (sec) | 100 mM | 250 mM | 500 mM | 1000 mM |
| 0 | 0.6 | 0.0 | 1.2 | 0.0 |
| 5 | 0.9 | 1.0 | 2.7 | 0.0 |
| 10 | 2.7 | 4.6 | 17.2 | 0.0 |
| 15 | 41.2 | 42.2 | 86.4 | 86.7 |
| 20 | 52.0 | 116.2 | 190.1 | 346.0 |
| 25 | 53.7 | 121.7 | 242.7 | 456.5 |
| 30 | 51.0 | 121.7 | 241.6 | 503.4 |
| 40 | 50.9 | 120.8 | 246.4 | 274.8 |
| 50 | 48.9 | 117.5 | 245.3 | 462.6 |
| 60 | 51.1 | 120.8 | 232.7 | 452.4 |

Figure 6:
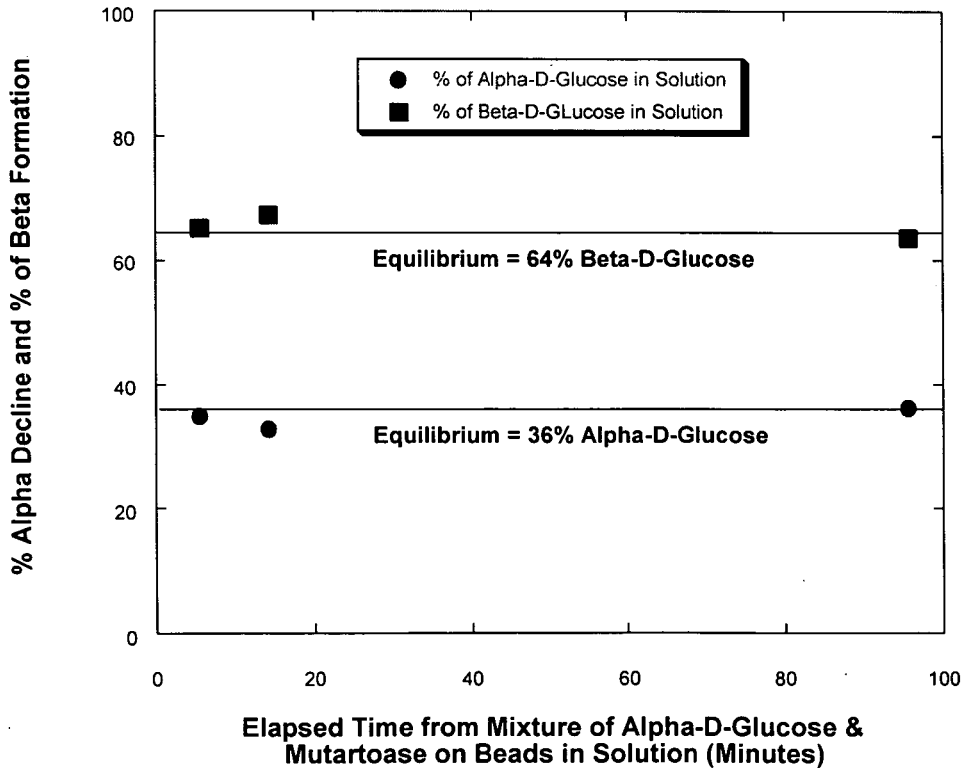
FIG. 6 shows the conversion of α-D-glucose to an equilibrium mixture of α-D-glucose and β-D-glucose in the presence of mutarotase immobilized on the surfaces of silica beads.

The third column containing mutarotase immediately converts α-D-glucose to β-D-glucose in a ratio of 36% α to 64% β. This is the equilibrium mixture that is achieved over time when placing α-D-glucose in solution. There is no available assay to distinguish between α and β-D-glucose in the effluent solution from the mutarotase column. Consequently mutarotase beads and α-D-glucose were placed in an NMR sample tube with $D_2O$ solvent and the quantities of α and β-glucose were determined by taking NMR spectrums over time. FIG. 6 shows the immediate response of the mutarotase on beads to form the equilibrium mixture of α and β-D-glucose from the starting α-D-glucose. This same response is expected in the mutarotase column.

The invention is now illustrated by a series of examples which show the behavior of the enzymatic cascade system described above. However, it should be understood that the invention is not intended to be limited to any specific embodiment.

EXAMPLES

Example 1

Figure 7:
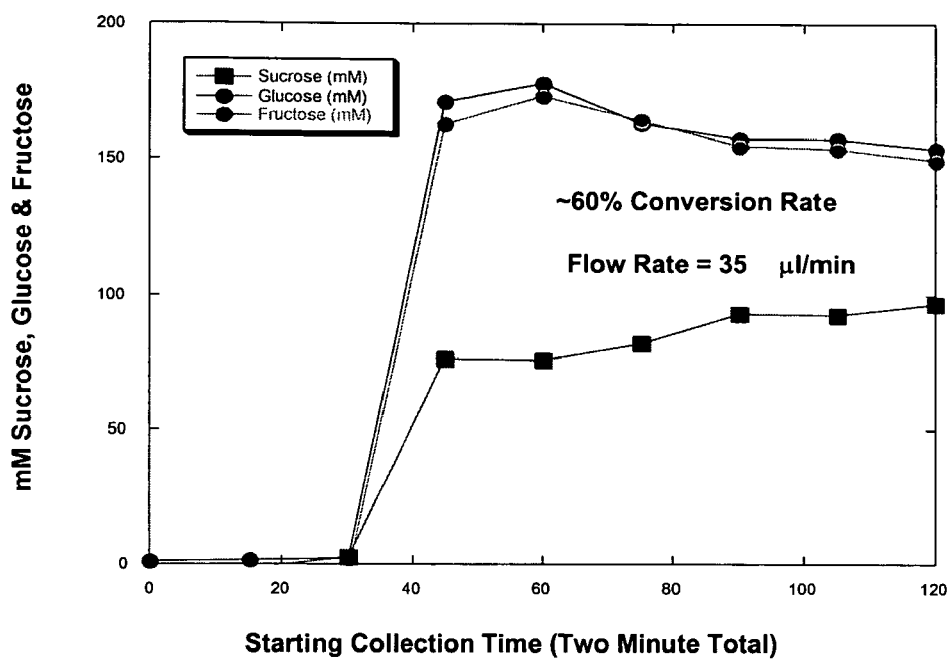
FIG. 7 illustrates the conversion of sucrose to glucose using three columns linked in series, each packed, respectively, with invertase, glucose isomerase, and mutarotase, wherein sucrose, in a pH 5.8 buffer, was flowed through the columns at a temperature of 47° C.

Although each enzyme has its own set of optimal pH and temperature conditions under which it performs best, we have obtained a 50% conversion of sucrose to glucose by placing three columns in series and providing a fuel stream with a pH=5.8 and 20mM $MgCl_2$ at a temperature of 47° C. This pH and temperature is an average of the ranges that the individual enzymes prefer. Order of columns is invertase→glucose isomerase→mutarotase. Conditions were determined by averaging all three enzyme optimal operating conditions. The data obtained is presented in TABLE 3 below and shown graphically in FIG. 7.

TABLE 3

Measured Concentration of Sucrose, Glucose and Fructose in Output Stream of the Cascade Series of Columns of the Present Invention at a pH = 5.8 and a temperature of 47° C.

| Collection Time (sec) | Sucrose Concentration (mM) | Glucose Concentration (mM) | Fructose Concentration (mM) |
|---|---|---|---|
| 0 | 0.0 | 1.2 | 0.0 |
| 15 | 0.0 | 1.5 | 0.0 |
| 30 | 2.5 | 2.0 | 0.0 |
| 45 | 76.1 | 171.0 | 163.0 |
| 60 | 75.5 | 178.0 | 173.1 |
| 75 | 81.8 | 163.5 | 164.6 |
| 90 | 93.2 | 157.4 | 155.0 |
| 105 | 92.4 | 157.5 | 153.7 |
| 120 | 96.8 | 154.0 | 149.6 |

Example 2

Figure 8:
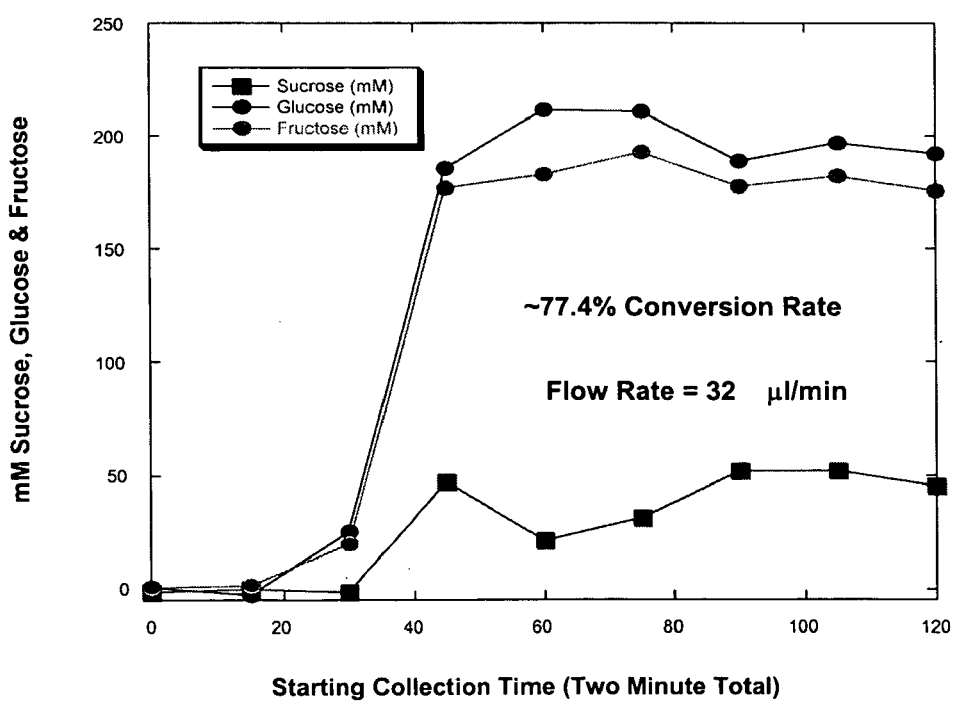
FIG. 8 shows the conversion of sucrose to glucose using three columns linked in series, each packed, respectively, with invertase, glucose isomerase, and mutarotase, wherein sucrose, in a pH 4.6 buffer, was flowed through the columns at a temperature of 46° C.

We have obtained, however, a 77% sucrose to glucose conversion yield by placing three columns in series and providing a fuel stream that uses the optimum conditions for the invertase enzyme with a pH=4.6 at a temperature of 46° C. As before the order of the columns was invertase→glucose isomerase→mutarotase. The optimal operating conditions for the invertase enzyme were used. The data obtained is presented in TABLE 4 below and shown graphically in FIG. 8.

TABLE 4

Measured Concentration of Sucrose, Glucose and Fructose in Output Stream of the Cascade Series of Columns of the Present Invention at a pH = 4.6 and a temperature of 46° C.

| Collection Time (sec) | Sucrose Concentration (mM) | Glucose Concentration (mM) | Fructose Concentration (mM) |
|---|---|---|---|
| 0 | 0.0 | 0.1 | 0.4 |
| 15 | 0.0 | 0.0 | 1.2 |
| 30 | 0.0 | 25.0 | 19.6 |
| 45 | 47.2 | 185.4 | 177.1 |
| 60 | 21.0 | 211.2 | 182.7 |
| 75 | 31.0 | 211.1 | 193.1 |
| 90 | 51.9 | 198.1 | 177.4 |

TABLE 4-continued

Measured Concentration of Sucrose, Glucose and Fructose in Output Stream of the Cascade Series of Columns of the Present Invention at a pH = 4.6 and a temperature of 46° C.

| Collection Time (sec) | Sucrose Concentration (mM) | Glucose Concentration (mM) | Fructose Concentration (mM) |
|---|---|---|---|
| 105 | 51.9 | 196.6 | 182.5 |
| 120 | 45.1 | 192.2 | 175.6 |

Example 3

Figure 9:
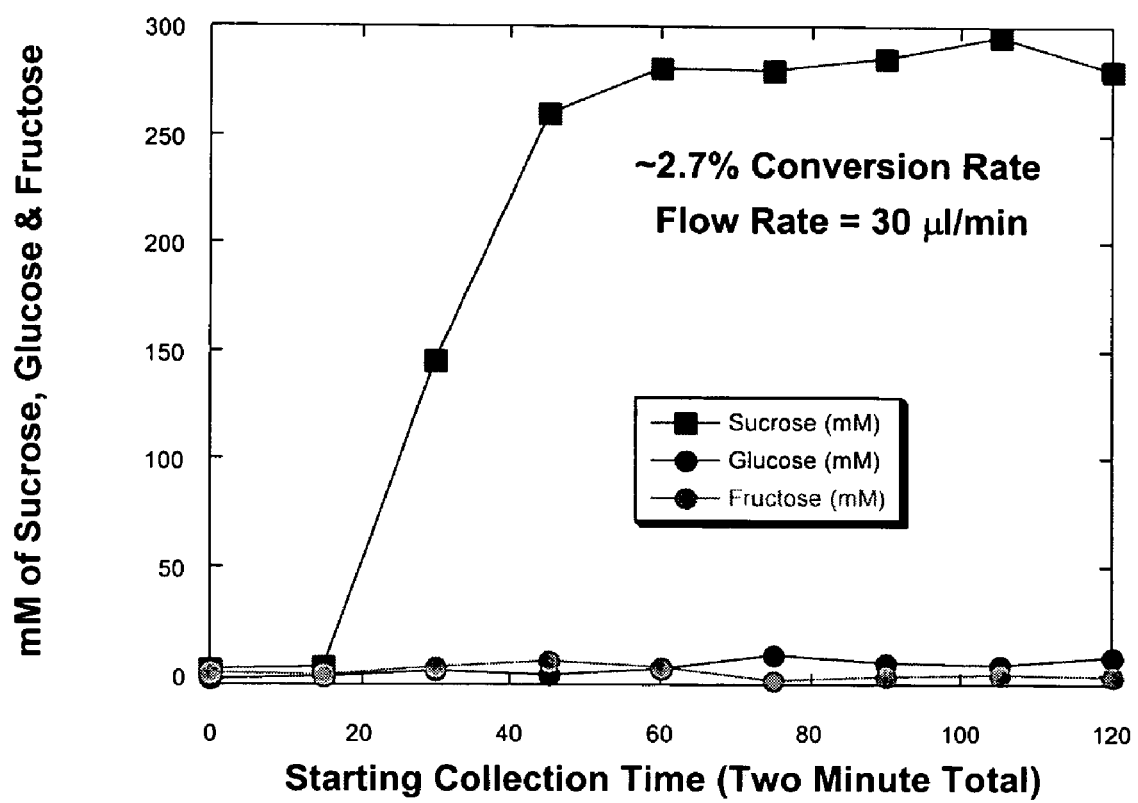
FIG. 9 shows the conversion of sucrose to glucose using three columns linked in series, each packed, respectively, with invertase, glucose isomerase, and mutarotase, wherein sucrose, in a pH 6.8 buffer, was flowed through the columns at a temperature of 62° C.

We have obtained only a 2.7% conversion of sucrose to glucose by placing three columns in series and providing a fuel stream that uses the optimum conditions for the glucose isomerase enzyme with a pH=6.8 and 20 mM $MgCl_2$ at a temperature of 62° C. The higher temperature needed for glucose isomerase optimum activity is detrimental to the invertase enzyme causing permanent inactivation and consequently a low conversion percentage. The data obtained is presented in TABLE 5 below and shown graphically in FIG. 9.

TABLE 5

Measured Concentration of Sucrose, Glucose and Fructose in Output Stream of the Cascade Series of Columns of the Present Invention at a pH = 6.8 and a temperature of 62° C.

| Collection Time (sec) | Sucrose Concentration (mM) | Glucose Concentration (mM) | Fructose Concentration (mM) |
|---|---|---|---|
| 0 | 2.8 | 0.0 | 0.7 |
| 15 | 3.7 | 0.0 | 0.0 |
| 30 | 145.6 | 1.5 | 3.2 |
| 45 | 259.5 | 0.0 | 6.1 |
| 60 | 280.4 | 2.2 | 3.3 |
| 75 | 279.5 | 8.4 | 0.0 |
| 90 | 285.2 | 5.5 | 0.0 |
| 105 | 295.1 | 4.1 | 0.0 |
| 120 | 279.6 | 7.5 | 0.0 |

Finally, while the invention has been described with respect to providing a source of simple glucose, it should be understood that while the invention applies generally to bio-reformation of complex sugars it also applies to other compounds including, but not limited to, fatty acids, triglycerides, cholesterols, urea, lactates, pyruvate, and the like which are substrates for different enzymes to undergo enzymatic conversion. Thus the enzymes to be immobilized on particles would be at least one of the group consisting of invertase, mutarotase, glucose isomerase, glucose oxidase, catalase, lactate enzymes, pyruvate enzymes, urease, and cholesterol enzymes. Further, it should be understood that the invention applies also to any other bio-reformation reaction which may be arranged to occur on a solid substrate.

Therefore, the present invention is, of course, in no way restricted to the specific disclosure of the specification or the drawings, but also encompasses any modifications within the scope of the appended claims.

What is claimed is:

1. A system for converting sucrose to, β-D-glucose, comprising:
   a reservoir comprising a solution of sucrose;
   pumping means in fluid communication with said reservoir;
   a first porous packed column comprising invertase, said first porous packed column-in fluid communication with said pumping means;
   a second porous packed column comprising glucose isomerase, said second porous packed column in fluid communication with said first porous packed column;
   a third porous packed column comprising mutarotase, said third porous packed column in fluid communication with said second porous packed column; and
   means for heating said first, second and third porous packed columns.

2. The system of claim 1, wherein the second porous packed column further comprises an $Mg^+$ stabilizer.

3. The system of claim 2, wherein the $Mg^+$ stabilizer comprises $MgCl_2$.

4. The system of claim 3, wherein $MgCl_2$ is present in an concentration of about 20 mM.

5. The system of claim 1, wherein:
   said first, second and third porous packed columns comprise inlet and outlet ends, wherein said first porous packed column inlet end is in fluid communication with said pumping means, said second porous packed column inlet end is in fluid communication with said first porous packed column outlet end; and said third porous packed column inlet end is in fluid communication with said second porous packed column outlet end.

6. The system of claim 1, wherein said pumping means is a positive displacement or a dynamic pump.

7. The system of claim 6, wherein said pumping means is selected from the group consisting of peristaltic pumps, reciprocating piston pumps, rotary gear pumps, helical screw pumps, rotary lobe pumps, gear-within-gear pumps, diaphragm pumps, progressing cavity pumps, and a vane pumps.

8. The system of claim 1, wherein the means for heating comprises electrically heating each of said first, second, and third porous packed columns.

9. The system of claim 8, wherein electrically heating said porous packed columns comprises wrapping the porous packed columns with heating tape.

10. The system of claim 1, wherein the means for heating comprises heating the porous packed columns by contacting said packed columns with a heated jacket.

11. The system of claim 10, wherein the heated jacket contains a circulating heated liquid.

12. The system of claims 8 or 10, wherein the porous packed columns are maintained at a temperature between about 43° C. to about 47° C.

13. The system of claim 1, wherein each of the first, second, and third porous packed columns comprise a glass chromatography column filled with a plurality of silica beads.

14. The system of claim 13, wherein the silica beads comprise a native surface having a plurality of aminated structures attached thereto.

15. The system of claim 14, wherein each of the plurality of aminated structures comprises an amine functional group attached to said native surface of the silica beads, and an amine group cross-linker attached to each of said amine functional groups, wherein said amine group cross-linker provides a site for protein reaction.

16. The system of claim 15, wherein the amine functional group is selected from the list consisting of aminopropyltriethoxysilane, aminopropyltrimethoxysilane, aminopropylmethyldiethoxysilane; aminopropylmethyldimethoxysilane; aminoethylaminopropyltriethoxysilane; aminoethylaminopropyltrimethoxysilane; aminoethylaminopropylmethyldimethoxysilane; diethylenetriaminopropyltriethoxysilane; diethylenetriaminopropyltrimethoxysilane; diethylenetriaminopropylmethyldiethoxysilane; diethylenetriaminopropylmethyldimethoxysilane; cyclohexylaminopropyltrimethoxysilane; haxanedoaminomethyltriethoxysilane; phenylaminomethyltriethoxysilane; phenylaminomethyltrimethoxysilane; diethylaminomethyltriethoxysilane; (dimethylaminomethyl)methyldimethoxysilane; and methylaminopropyltrimethoxysilane.

17. The system of claim 15, wherein the plurality of amine functional groups comprise an amino alkyl alkyloxy silane.

18. The system of claim 17, wherein the plurality of amine functional groups comprise 3-aminopropyltriethoxysilane.

19. The system of claim 15, wherein the amine group cross-linker is selected from the group consisting of formaldehyde, glutaraldehyde, mono- and di-aldehyde PEG, and bis(imido esters), bis(succinimidyl esters), diisocyanates and diacid chlorides.

20. The system of claim 19, wherein the amine group cross-linker comprises a mono- or di-aldehyde.

21. The system of claim 20, wherein the amine group cross-linker is glutaraldehyde.

22. The system of claim 1, wherein the solution of sucrose comprises a buffer fluid having a pH between about 4.6 and about 5.8.

* * * * *